United States Patent [19]

Cathey et al.

[11] Patent Number: 5,503,985
[45] Date of Patent: * Apr. 2, 1996

[54] DISPOSABLE DEVICE FOR DIAGNOSTIC ASSAYS

[76] Inventors: Cheryl A. Cathey, 953A Roble Ridge, Palo Alto, Calif. 94306; Henry L. Schwartz, 2579 Union St., San Francisco, Calif. 94123; Tom Saul, P.O. Box 372, Moss Beach, Calif. 94018; Jeffrey D. Langford, 1172 Terra Nova Blvd., Pacifica, Calif. 94044

[*] Notice: The portion of the term of this patent subsequent to Mar. 21, 2012, has been disclaimed.

[21] Appl. No.: 179,749

[22] Filed: Jan. 7, 1994

Related U.S. Application Data

[63] Continuation-in-part of Ser. No. 19,469, Feb. 18, 1993.
[51] Int. Cl.$^6$ .................. G01N 33/542; G01N 33/543; G01N 33/558
[52] U.S. Cl. .................. 435/7.9; 422/55; 422/57; 422/58; 435/7.92; 435/7.93; 435/7.94; 435/810; 436/164; 436/172; 436/514; 436/518; 436/524; 436/527; 436/528; 436/537; 436/805; 436/807; 436/808; 436/810
[58] Field of Search .................. 422/55, 57, 58, 422/64; 435/7.9, 7.92, 7.93, 7.94, 810, 973; 436/514, 518, 524, 527, 528, 800, 805, 807, 808, 810, 164, 172, 537

[56] References Cited

U.S. PATENT DOCUMENTS

| | | | |
|---|---|---|---|
| 4,426,451 | 1/1984 | Columbus | 422/58 |
| 4,918,025 | 4/1990 | Grenner | 422/56 |
| 5,028,142 | 7/1991 | Ostoich et al. | 356/427 |
| 5,053,197 | 10/1991 | Bowen | 422/57 |
| 5,061,446 | 10/1991 | Guigan | 422/64 |
| 5,079,142 | 1/1992 | Coleman et al. | 422/56 |
| 5,133,937 | 7/1992 | Frackleton et al. | 422/67 |
| 5,167,922 | 12/1992 | Long | 422/58 |
| 5,207,988 | 5/1993 | Lucas | 422/73 |

FOREIGN PATENT DOCUMENTS 0430248 5/1991 European Pat. Off. .

*Primary Examiner*—Toni R. Scheiner
*Assistant Examiner*—Christopher L. Chin
*Attorney, Agent, or Firm*—Bertram I. Rowland; Bret E. Field

[57] ABSTRACT

A disposable diagnostic device and method of its use are provided. The device comprises a housing containing first and second flow paths orthogonal to each other. The first flow path commences at a sample addition port and continues through a transport channel which feeds sample to an incubation area by means of capillary flow. The incubation area comprises a signal producing system and is underneath an optically-clear window. The first flow path terminates in a top waste reservoir which receives sample and wash fluid. The second flow path begins on one side of the incubation area at an inlet port over a side reagent reservoir. Liquid flows along the second flow path from the side reagent reservoir across the incubation area into the side waste reservoir. The incubation area may comprise agitation means for homogenous dispersion of reagent into liquid. Various reagents of a signal producing system may be contained within the device and the necessary liquids added automatically by appropriate instrumentation, so as to have the assay carried out automatically, without technician involvement, providing an accurate and sensitive determination.

22 Claims, 6 Drawing Sheets

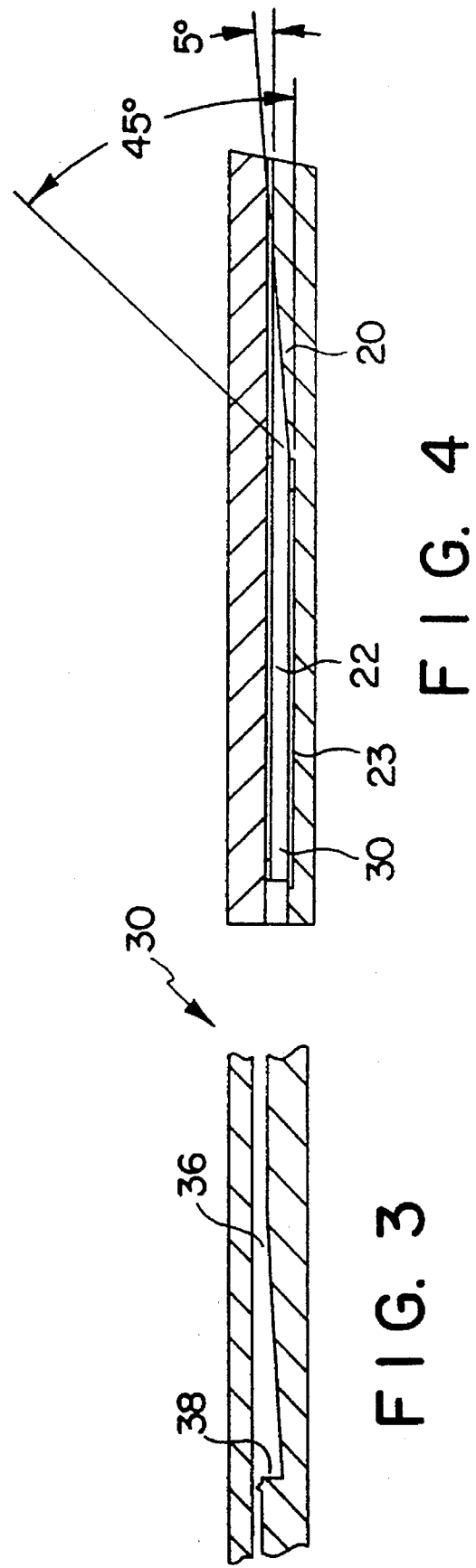

DISPOSABLE DEVICE FOR DIAGNOSTIC ASSAYS

CROSS-REFERENCE TO RELATED APPLICATIONS

This application is a continuation-in-part of application Ser. No. 08/019,469, filed Feb. 18, 1993.

INTRODUCTION

1. Technical Field

The field of this invention is disposable diagnostic devices.

2. Background

Despite the numerous strides that have been made in the last two decades in the development of diagnostic reagents and instruments, efforts continue to make diagnoses more accurate, simpler, and more available to non-technical personnel in a wide variety of environments. There is continuing interest in being able to carry out individual assays by non-technical personnel at such sites as doctor's offices, clinics, the home, rest homes, and the like. In order to ensure that non-technical individuals may accurately perform these assays, it is essential that the protocols be simple and that there be few, if any, measurements. Further, the readings must be relatively automatic. For this purpose, it is desirable to have a disposable device which can be used individually for each assay determination and then discarded.

In clinical laboratories, there are many opportunities for measuring an analyte in an individual assay determination. Frequently, a particular assay procedure may be determined only a few times in any given day. Under such circumstances, individual assays will be the most efficient method of performing a particular assay procedure. When a disposable assay device that requires minimal input from the operator is employed, significant savings in cost may be achieved. Cost savings result from the fact that highly skilled technicians will not be required to operate the device.

There is, therefore, a continuing need for disposable devices capable of performing individual assay protocols. These devices should require minimal measurement and input from the operator. Thus, the disposable devices should provide the various reagents necessary for a particular assay determination. The devices should also allow for sensitive and accurate quantification of the amount of analyte in a particular sample.

Long-standing difficulties with disposable diagnostic devices have included problems of non-specific effects due to inefficient mixing of reagents, inadequate washing of non-specifically bound reagents from detection areas, inaccurate analyte detection due to inhomogeneous mixing of reagent and sample, as well as problems controlling fluid flow through the devices.

RELEVANT LITERATURE

Relevant literature includes U.S. Pat. Nos. 5,096,836; 5,164,598; 5,053,197; and 5,051,237. Relevant literature also includes European Patent Application Nos. 0,394,041; and 0,430,248.

SUMMARY OF THE INVENTION

Devices and methods are provided for the quantification of analyte in a sample using a disposable diagnostic device. The disposable device generally comprises a housing containing two flow paths which are orthogonal to one another. The first flow path commences at a sample application port, continues along a transport capillary channel into an incubation area and terminates in a top waste reservoir. The second flow path commences at an inlet port, commences through a side reagent reservoir across the incubation area and terminates in a side waste reservoir. The first flow path may include agitation means in the incubation area for homogenous dispersion of dry reagent in the sample liquid.

In using the subject device to assay for a particular analyte, liquid sample is introduced into the first flow path followed by introduction of liquid into the second flow path. After a predetermined time, a first reading followed by subsequent readings may be made. The amount of analyte is determined by comparison of the first and subsequent readings, or with comparison to a control.

BRIEF DESCRIPTION OF THE FIGURES

FIG. 3 is a cross-section view of the disposable device along line 3—3 in FIG. 1.

FIG. 4 is a cross-section view of the disposable device along line 4—4 in FIG. 1.

DESCRIPTION OF THE SPECIFIC EMBODIMENTS

Figure 1:
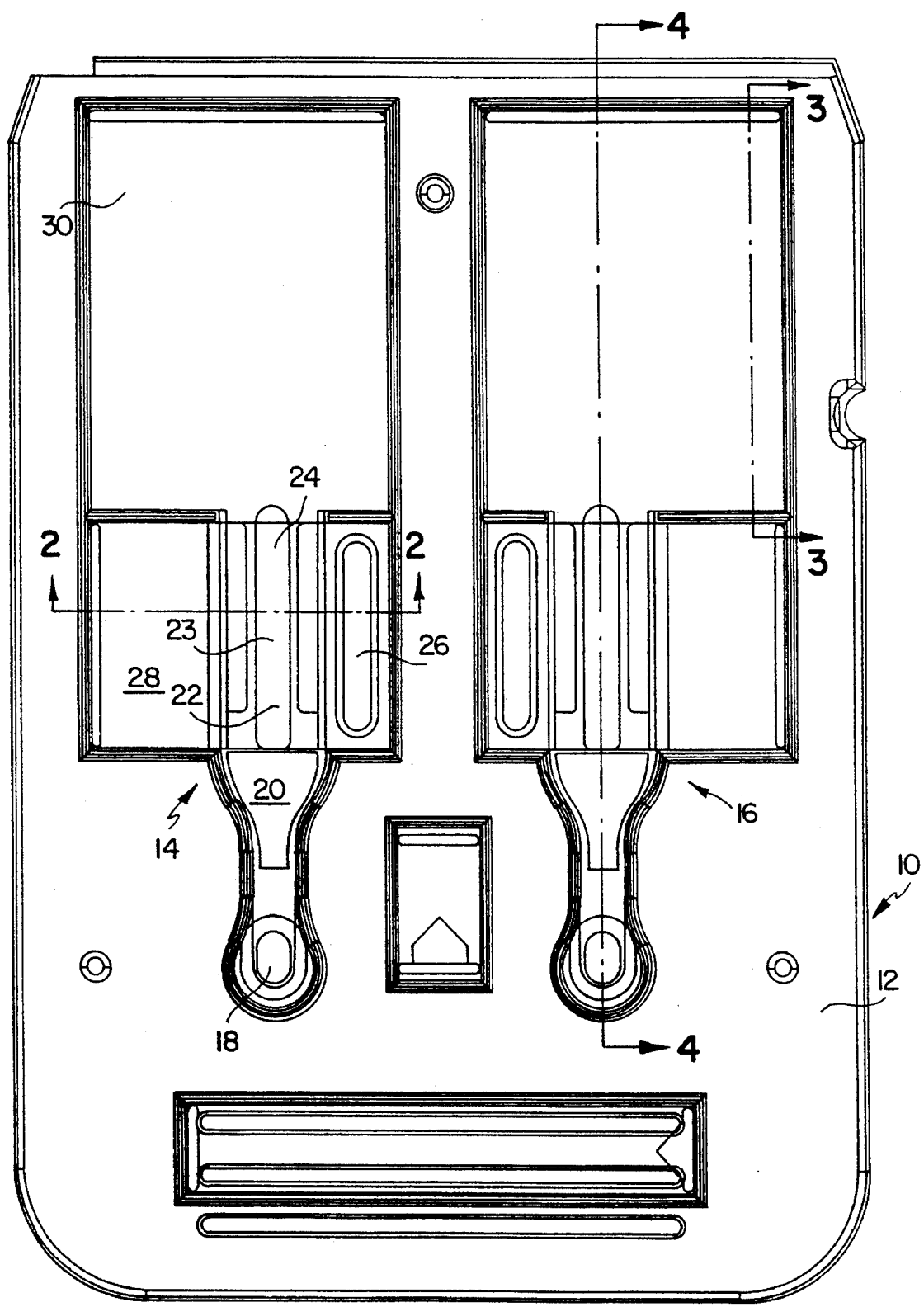
FIG. 1 is a plan view of the disposable device.

A disposable device and methods for its use are provided for optical determination, particularly fluorescent determination, of an analyte. The device is a housing containing two flow paths orthoganol to one another that intersect in a sample incubation area. The first flow path commences at a sample application port, continues along a transport capillary to an incubation area and terminates in a top waste reservoir. The second flow path commences at a side reagent port through a side reagent reservoir, continues across the incubation area and terminates in a side waste reservoir. The device finds application in assays for the presence and quantity of particular analytes in liquid samples. In further describing the subject device and methods, the first and second flow path's will be discussed in turn, followed by a discussion of the assay used in the subject device.

The first flow path commences at the sample port. A sample transport channel having upper and lower walls, which are sufficiently close so as to transport liquid sample by capillary action, joins the sample port to the incubation area. The transport channel may serve a plurality of purposes besides serving as the conduit for movement of the sample. Various reagents may be present in the channel, either diffusibly or non-diffusibly bound to the walls. For example, antibodies may be bound to the walls which would serve to remove one or more components of the sample, e.g. cells, interfering components, etc. Chemical reagents may be present to change the pH, redox potential or other characteristics of the sample. In this way the sample which is introduced into the incubation area may be different from the sample introduced at the sample port.

Downstream from the sample transport channel is the sample incubation area having top and bottom surfaces spaced such that there is capillary flow through the incubation area. On the top surface is an optically clear window and on the bottom surface is a platform. Flanking the platform on one side of the incubation area is a side reagent reservoir and on the other side is a side waste reservoir.

Directly below the optically clear window on the top surface of the incubation area is an assay measurement surface. The particular assay measurement surface present will depend on the signal producing system used in the disposable device. One signal-producing system is described in U.S. Pat. No. 5,156,810, the disclosure of which is incorporated herein by reference. This system employs a polymerized lipid layer which is highly fluorescent upon irradiation with light within an appropriate wavelength range. Proximal to one face of the layer is a member of a specific binding pair, where the pair consists of ligand and receptor. The lipid layer is applied to the assay measurement surface. Various techniques may be employed for applying a lipid layer to the assay measurement surface.

The platform supports one or more members of a signal-producing system. Members of the signal producing system which may be present on the platform include dry reagent that comprises a member of a specific binding pair. This specific binding pair member is cross-reactive with, i.e. competitive, or complementary to, i.e. capable of binding to, the specific binding pair member of the lipid layer. The reagent specific binding pair member is conjugated to a label which provides for a detectable signal in conjunction with the lipid layer. Where the signal from the lipid layer is an optical signal, the labeled conjugate will directly or indirectly modulate the optical signal in relation to the amount of analyte which is in the liquid sample.

In a preferred embodiment, the label will be an enzyme which acts on a substrate to produce a product which can interact with the membrane layer. The product may be a fluorescer, a quencher, a dye which absorbs light in the wavelength range of irradiation, or other compound which may serve to modulate the observed optical signal in relation to the amount of analyte in the sample. At an appropriate time, one can introduce substrate from the side reagent reservoir to the incubation area in an orthogonal manner to the direction of flow of the sample along the second flow path, so as to wash the platform, as well as provide substrate.

Alternatively, one may use labels other than an enzyme. The choice of other labels will depend upon the sensitivity desired, the manner of detection, the nature of the sample, as well as the analyte, and the like. Thus, one may use fluorescent labels, which can provide for channeling of the energy from the membrane label to the fluorescer, so as to provide a substantial Stokes shift, whereby the emitted light is substantially displaced from the light absorbed by the membrane and light which would otherwise be emitted frown the membrane. One may also use fluorescers which have significant delay times, such as chelated lathanides, so that upon irradiation, one delays the reading to allow for other fluorescence to die down. Further, the label may be an enzyme which acts on a substrate which provides an optical signal representative of the amount of analyte.

In one embodiment, the platform is separated from the side reagent reservoir by a wall that slopes down from the plane of the platform into the side reagent reservoir, typically at an angle of 90°. The platform is separated from the side waste reservoir by a wall that slopes down from the plane of the platform to the floor of the side waste reservoir at a more gradual angle, typically about 50°.

In one embodiment of the invention, agitation means may be provided to ensure homogenous mixing of liquid present in the incubation area at any given time. Agitation means may comprise any convenient means which creates sufficient turbulence in the incubation area so that dry reagent present in the incubation area is homogeneously distributed throughout the liquid sample. Agitation means may include airflow, shaking, ultrasonic techniques or a mechanical mixing implement.

Where the agitation means is a mechanical agitation means, in one embodiment on the platform in the incubation area will be at least one trough that houses the mechanical mixing implement. This trough may extend the length of the platform. The depth and width of the trough will be dictated by the particular mechanical mixing implement employed. The trough will be deep enough so that the mixing implement is fully contained within the trough. For example, if 0.039 in. diameter steel balls are used as the mixing implement, the depth of the trough can be 0.042 in. The trough will be wide enough to provide free movement of the mixing implement. The mixing implement trough may comprise dry reagent of the signal producing system in addition to the mixing implement.

On either side of the mixing implement trough and running parallel with the mixing implement trough may be troughs comprising dry reagent of the signal producing system. Similarly to the mixing implement trough, these troughs may extend the length of the incubation area.

The mechanical mixing implement may be of any convenient shape which can be moved to provide mixing of the contents of the incubation area. Examples of mechanical mixing implements suitable for use as agitation means include magnetic pins, magnetic dumbbells, perforated magnetic sheets and magnetic discs with fins. Preferably, two stainless steel balls will serve as the mixing implement. The mixing implement will be constrained in the trough by the top surface of the incubation area. In determining the dimensions of the mixing implement, the mixing implement should be small enough to fit within the incubation area. Further, movement of the mixing implement should not result in displacement of fluid from the incubation area to other areas of the device.

The mechanical mixing implement may be moved by any convenient means. Typically, with paramagnetic materials, an applied magnetic field moved above or below the device will provide the force necessary to move the mixing implement. Alternatively, the device may be moved over a stationary magnetic field.

The platform comprising the mixing implement will be separated from the side reagent reservoir by a rectangular cross section shaped ridge extending to a position just below the bottom surface of the upper wall or ceiling. Thus, a capillary flow space is provided for fluid flow between the side reagent reservoir and the incubation area. The platform is separated from the side waste reservoir by a trapezoidal cross section ridge which again extends to a position just below the ceiling over the incubation area, thereby providing for fluid flow over the trapezoidal cross section shaped wall into the side waste reservoir.

In a preferred embodiment, instead of having side ridges that extend to just below the ceiling of the incubation area, the platform may have more shallow ridges on either side of the path of movement of the mixing implement. These shallow ridges will serve as a guide for the mixing implement as it moves the length of the incubation area.

Downstream from the incubation area will be the top waste reservoir which will serve to receive the sample and washing solutions which are introduced into the sample port, flow through the transport channel and over the incubation area. For most assay determinations, the volume of the top waste reservoir ranges from about 30 µl to about 2 ml. Thus, the top waste reservoir receives fluid from the incubation area, and serves as a storage reservoir for that liquid.

The second flow path of the device commences at an inlet port, flows through the side reagent reservoir, flows across the incubation area and terminates in the side waste reservoir. The side reagent liquid addition port lies directly above the side reagent reservoir and provides for the introduction of liquid into the side reagent reservoir. The side reagent reservoir will generally have a volume of about 10 µl to 500 µl. Coating a wall or walls of the side reagent reservoir may be a member of the signal producing system, e.g. enzyme substrate, where the label is an enzyme. Alternatively, on the floor of the side reagent reservoir may be a trough which comprises the reagent. The trough may be any convenient shape, including oval, rectangular or the like.

Fluid flows over the ridge separating the side reagent reservoir and onto the platform of the incubation area. The flow path continues across the incubation area and terminates in the side waste reservoir. The side waste reservoir has a volume ranging from about 10 µl to 1 ml. Thus, the second flow path of the device flows orthogonal to the first flow path, intersecting the first flow path over the incubation area. The side waste reservoir serves as an end point for the second flow path, as well as a reservoir for fluid which has flowed through the second flow path.

The device may also comprise a capillary valve located adjacent to the incubation area at various positions along the first and second flow paths for enhanced control over liquid flow through the incubation area. Thus, the capillary valve may be positioned in the second flow path between the side reagent reservoir and the incubation area to control the flow of liquid from the side reagent reservoir into the incubation area. Further, a capillary valve may be positioned in the first flow path to control fluid flow into and/or out of the incubation area.

The capillary valve consists of a control capillary that intersects the subject flow path, conveniently at right angles. The depth of the control capillary will be greater than the depth of the intersected flow path. The control capillary is designed so that capillary flow in the control capillary is not impeded at the intersection with the flow path. However, capillary flow in the flow path is impeded at the intersection when the control capillary is void of liquid because of the sharp interuption in the depth of the flow path. Only when the control capillary is full is capillary flow in the intersected flow path not impeded. Thus, fluid flow through the device can be controlled by either filling or emptying the control capillary with liquid.

The device which is employed can be varied as to size, usually being at least about 1 cm×3 cm and not more than about 4 cm×8 cm, preferably having the smaller dimension in the range of about 1–3 cm and in the longer direction by about 3–8 cm. While for the most part, the device may be any convenient shape, conveniently, it will be rectangular where the edges may be modified by rounding, cutting the corner(s), or other modification which will allow for easy handling and adapting the device for use in conjunction with an automated instrument. The thickness of the device will generally vary from about 1–5 mm, more usually about 1.5–3 min.

The housing of the device will usually be made of two plates, which will be sealed together. Conveniently, the top housing plate will serve primarily as a cover and provide the ports and optical window(s). The bottom housing plate will provide the various structures necessary for the reservoirs and channels associated with the device. Therefore, the plate into which the various reservoirs and channels are molded will usually be thicker than the cover plate, generally about 1.5–2-fold thicker than the cover plate.

The plates may be molded out of various plastics which allow for reasonably accurate tolerances, can withstand the various chemicals involved, and will allow for the presence of an optically-clear area. Plastics which fulfill these requirements include acrylate, polystyrene, polycarbonate, SAN, ABS, etc.

The two flow paths of the device having been described, an assay suitable for use in the device will now be discussed. In carrying out an assay, one may assay any type of liquid, which frequently may be used directly or may be subjected to prior treatment, depending upon the nature of the liquid and the analyte of interest. The liquid may contain a sample or be a sample from any source, such as a physiological source, e.g. blood, serum, plasma, urine, saliva, spinal fluid, lysate, etc.; sample of ecological interest, e.g. water, soil, waste streams, organisms, etc.; food, e.g. meat, dairy products, plant products, etc.; drugs or drug contaminants in processing; or the like.

The analyte may be any type of compound, e.g. small organic molecules, peptides and proteins, sugars, nucleic acids, lipids and combinations thereof, naturally occurring or synthetic or combinations thereof, so long as there is a complementary binding member. The analyte may be any compound which can be detected and is a member of a specific binding pair, either ligand or receptor. The term "receptor" is used arbitrarily, since its origin had to do with surface membrane proteins, where the compound which bound to the surface membrane protein was referred to as a ligand. Receptors include naturally occurring receptors, e.g. enzymes, lectins, surface membrane proteins, antibodies, recombinant proteins, etc., synthetic receptors, nucleic acids, etc. For the purpose of the subject invention, it is sufficient that two molecules have a significant affinity for each other, where the binding constant will usually be at least about $10^7$ $mol^{-1}$ and one may choose to refer to either member as the receptor. Compounds of interest have to some degree been indicated by indicating the various sample sources. The analytes will frequently include drugs, both naturally-occurring and synthetic, various components of animals, including humans, such as blood components, tissue components, and the like; microorganisms, such as bacteria, fungi, protista, viruses, and the like; components of waste streams or products or contaminants of such products in commercial processing; components in the environment, particularly contaminants, such as pesticides, microorganisms, and the like.

Depending upon the nature of the sample, the sample may be subjected to prior treatment, such as extraction, distillation, chromatography, gel electrophoresis, dialysis, dissolution, centrifugation, filtration, cell separation, and the like. For blood, one may wish to remove red blood cells to provide plasma or serum but their removal is not necessary. Various media may be employed, which will allow for providing for a sample solution or dispersion which can be used in the subject device.

After appropriate pretreatment, if any, the sample in liquid form is then introduced into the sample port. The device may be designed to accept a broad range of volumes as the sample. Thus, the volume of sample may range from about 1 μl to about 0.5 ml, more usually from about 10 μl to 250 μl, preferably from about 25 μl to 170 μl. The sample is drawn from the sample application port by capillary action through a sample transport channel dissolving and/or reacting with any reagent present in the transport channel.

As the sample flows into the incubation area, it combines with the dry reagent in the incubation area. The dry reagent may be provided in the transport channel, but will usually be present, at least in part, in the incubation area. The dry reagent, i.e. the labeled conjugate, will be dissolved by the sample and reaction will occur between complementary members, one member of which is located on the fluorescent lipid membrane. The assay protocol may involve competition or cooperation. In the case of competition, the conjugate will bind to either the analyte or binding sites on the membrane surface. By having a limited number of conjugate molecules, the number of conjugate molecules which can bind to the membrane will be inversely proportional to the number of molecules of analyte in the sample. Thus, the number of labels which become bound to the surface will be inversely proportional to the number of analyte molecules in the sample. This approach will normally be employed with small analytes, particularly haptenic analytes, where the analyte can only bind to a single receptor.

By contrast, with larger analytes, which are polyepitopic, one has the opportunity for two receptors to bind simultaneously. In this way, the analyte may serve as a bridge between the complementary binding member bound to the membrane and the complementary binding member which is labeled. One may also use the competitive protocol, by having the specific binding pair member of the conjugate capable of competing with the analyte for binding to the membrane.

After sufficient time for substantially complete reaction of the analyte in the incubation area, so that the member of the specific binding pair present in the sample, the analyte, can bind to the complementary member of the membrane or reagent, the incubation area, particularly the lipid membrane, may then be washed. A buffered aqueous solution may be used which is appropriate for maintaining the binding of the specific binding pair members. Usually, the volume of the wash solution will be at least about equal to the volume of the sample and may be 10-fold more or greater, usually not more than about 7-fold more or greater, and preferably at least about 2-fold greater.

Where an enzyme is the label, it is necessary to provide substrate for the enzyme to provide an enzyme product, so as to modulate the fluorescence signal provided by the membrane. The side reagent reservoir to one side of the incubation area will typically house this substrate. The side reagent reservoir is flooded by addition of liquid to the inlet port, so as to dissolve the substrate and drive the liquid comprising the dissolved substrate along the second flow path into the incubation area, and to some degree into the top waste reservoir.

There will be resistance to flow into the top waste reservoir at this time, due to the need to displace the fluid already present in that reservoir, which has resulted in substantially complete filling of the reservoir during the previous wash. In addition, the depth of the top reservoir may increase slightly at the far end away from the incubation area. This increase in depth increases the capacity of the top waste reservoir. However, when the fluid fills to the far end of the top waste reservoir, the driving force decreases with the increasing depth, so as to reduce the capillary force driving the liquid into this area. The added resistance to flow towards the top waste reservoir and the decrease in capillary driving force in the direction of the top waste reservoir offset the decrease in the capillary driving force of flow into the side waste reservoir, and the fluid begins to flow over the 50° slope into the side waste reservoir. This lateral flow washes out any residual sample that was at the edges of the incubation area and fills the incubation area with substrate. The enzyme present in the incubation area bound to the lipid membrane may then react with the substrate to provide for the appropriate signal.

The assay measurement surface is irradiated through the optically clear window above the incubation area, so as to excite the membrane. The optical signal, e.g. amount of fluorescent light which is emitted from the incubation area, is collected and counted. If desired, the optical signal is compared to a control value with a known amount of analyte, including no analyte. Alternatively, following the buffer washing step or steps, an initial reading of the film's optical properties may be taken and compared with the film's optical properties following exposure to reagent from the side reagent reservoir. This comparison may then be related to the amount of analyte in the sample. A single timed measurement, or a plurality of measurements to determine a rate, may be made.

Where the device includes agitation means for producing turbulence in the incubation area, the assay procedure further comprises the additional steps of creating turbulence in the incubation area at various times during the assay protocol. Thus, when the sample flowing along the first flow path reaches the incubation area, the sample will be agitated for a sufficient time to provide for homogenous dispersion of the dry reagent into the sample liquid. For example, where the agitation means is a mechanical means comprising two steel balls that are moved through application of an applied magnetic field, the steel balls will be rotated about each other and moved the length of the trough to sufficiently disperse the reagent in the liquid.

Similarly, when wash fluid is present in the incubation area, turbulence may be produced in the wash fluid to sufficiently disperse non-specifically bound reagent and analyte. When the wash fluid progresses along the first flow path to the top waste reservoir, non-specifically bound analyte and reagent will be removed from the incubation area.

Where the disposable device comprises a mixing implement, the fluid is constrained over the platform by the vertical sided ridge separating the side reagent reservoir from the incubation area and the trapezoidal cross section ridge separating the side waste reservoir from the incubation area.

The various applications of the fluid to the disposable device can be conveniently carried out automatically with an appropriate instrument. Thus, the instrument may measure the sample and wash volumes introduced into the device, time the incubations, maintain constant temperature, and take the reading, as appropriate. With the enzyme reaction, usually the reading will be timed, or two or more readings will be taken at a predetermined interval. Conveniently, when the applications of the disposable device are carried out in an automatic instrument, the disposable device may comprise an additional trough for receiving priming fluid used to prime conduits in the instrument prior to running the actual analyte assay procedure.

Where the device comprises a capillary valve to enhance control over fluid flow in the device, the control capillary will be filled and emptied at appropriate times. Filling and emptying of the control capillary may be accomplished by the instrument in which the disposable device is used.

The membrane on the assay measurement surface may be divided up into a plurality of sections, where each section may have the same or different specific binding pair member. In this way, the sample may be assayed simultaneously for a number of different analytes. Depending upon the nature of the different analytes, the same or different conjugates would be present in the incubation area. The assay could be carried out in the same way, except at the time of reading, one would specifically address different regions of the membrane to identify the fluorescence coming from each of the individual regions.

For further understanding of the invention, the drawings will now be considered.

In FIG. 1, the device 10 has a housing 12. The device is shown with first and second assay members, 14 and 16. It will be understood that each of the members are the same, except are shown as mirror images. Therefore, only the left-hand member 14 will be discussed.

The first flow path in the device commences at sample port 18 which connects with transport channel 20. The spacing in the transport channel 20 will generally be from about 0.001 to 0.100 in., usually from about 0.002 to 0.020 in. The transport channel 20 transports the sample or other fluids introduced into the sample port 18 to the incubation area 22.

The incubation area 22 provides for a number of functions. It is the site where the chemistry occurs, where one has the optically-responsive layer on the upper surface 24. Opposite to the upper surface, on the bottom surface, is the incubation platform 23, which is spaced apart from the upper surface 24. Platform 23 may be coated with dry reagent(s) which serves to react with, or compete with, the analyte, so that the amount of reagent that becomes bound to the membrane will be related to the amount of analyte in the sample. The spacing in the incubation area will be about 0.002 to 0.050 in., generally from about 0.005 to 0.015 in.

Where a substrate is necessary, the substrate will be stored in the side reagent reservoir 26. On the side of platform 23 opposite the side reagent reservoir 26 will be side waste reservoir 28. Therefore, a main capillary channel comprising the first flow path begins at sample port 18 and extends through transport channel 20 and incubation area 22 and terminates in top waste reservoir 30.

Figure 2A:
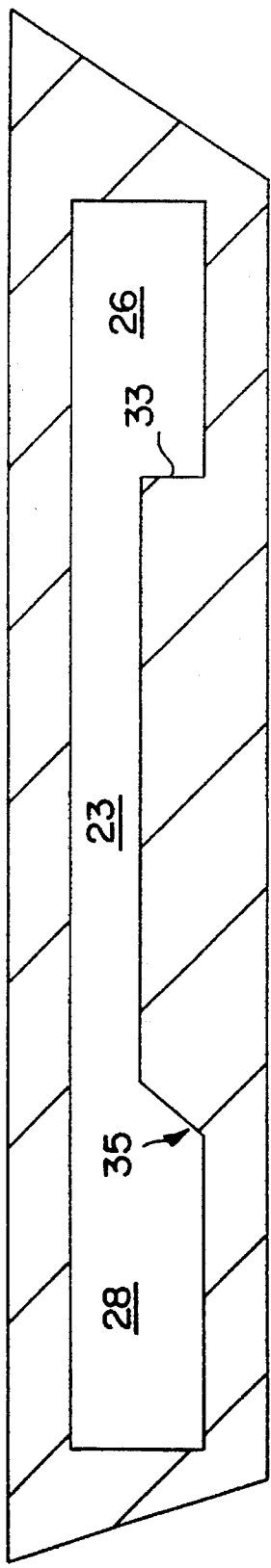
FIG. 2(a) is a cross-section view along line 2—2 in FIG. 1 of the disposable device without the mixing implement.

FIG. 2(a) is cross-section along line 2—2 in FIG. 1 of the disposable device that does not comprise a mixing implement trough. The side reagent reservoir 26, which may store soluble reagent, has a wall 33 which is set at a steep angle, conveniently a 90° angle in relation to platform 23 and the bottom of reagent reservoir 26. By contrast, the wall 35 between platform 23 and side waste reservoir 28 will be at a more shallow angle, conveniently at about 50° to the floor of the side waste reservoir 28.

Figure 2B:
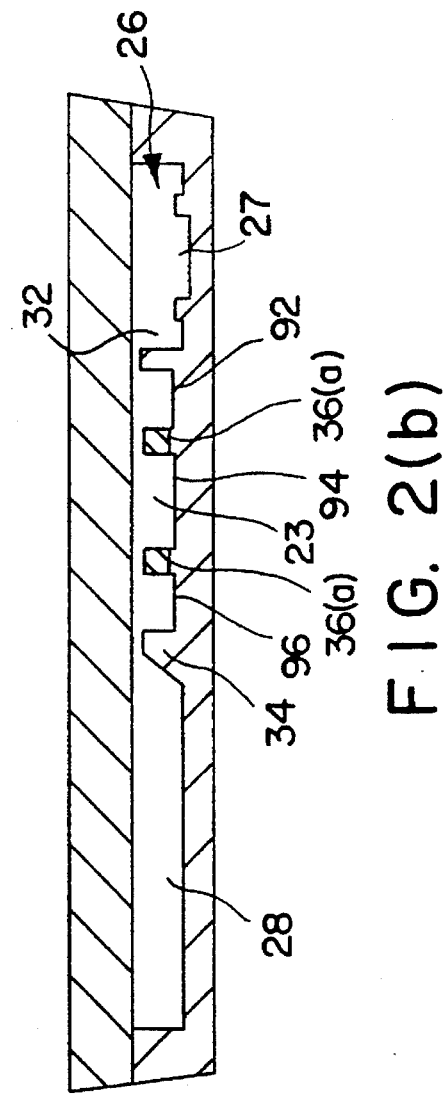
FIG. 2(b) is a cross-section view along line 2—2 in FIG. 1 of the disposable device with the mixing implement trough.

FIG. 2(b) is a cross-section along line 2—2 in FIG. 1 of the disposable device that comprises a mechanical mixing implement. The side reagent reservoir 26 comprises a substrate trough 27 which serves as a storage location for substrate. The side reagent reservoir has vertical ridge 32 which is at a steep angle, conveniently a 90° angle, in relation to platform 23 and the bottom of side reagent reservoir 26. The side waste reservoir 28 opposite the side reagent reservoir is separated from the platform 23 by a ridge 34 having a trapezoidal cross section, where the side of the ridge descending to the floor of the side waste reservoir will be at a more shallow angle, conveniently at about 50°. Platform 23, is divided into mixing implement trough 94, and dry reagent troughs, 92 and 96. Separating the mixing implement trough from the dry reagent troughs are ridges, 36(a) and 36(b), which range in height from about 0.005 in. to 0.01 in. so as not to impede forward liquid flow along the first flow path.

Where the disposable device does not comprise a mixing implement, as in FIG. 2(a), as the depth of the capillary flow channel increases, the capillary force that drives the flow decreases. With a 50° slope, the depth of the capillary increases very quickly over a short distance, thus decreasing the capillary force quite drastically over the same short distance. With a 90° slope, the depth of the capillary changes instantaneously, thus causing a discontinuity in the capillary force which effectively stops the flow over that edge. Thus, the flow of fluid is constrained on either side of the platform 23 by a sharp decrease in capillary force. However, the depth of the capillary channel does not change in the forward direction (toward the top waste reservoir), so the capillary driving force in that direction remains constant. Thus the flow of the sample is unconstrained in the forward direction.

When a buffered wash solution is introduced through the sample port 18, the buffer displaces the sample and the sample and buffer flow into the top waste reservoir 30. Again, the flow is constrained on both sides of the platform due to a drop in the capillary force, but is unconstrained in the forward direction. The addition of buffer in the sample application port washes most of the sample into the top reservoir.

When buffer is added to the side reagent reservoir through the inlet port, the reagent is rehydrated and flows over the platform area and forces fluid into both the top and side waste reservoirs. The fluid flows over the 50° angle into the side waste reservoir at this point, but not earlier during the sample addition step, because there is now added resistance to flow into the top waste reservoir due to the fact that this reservoir is either full or nearly so. This increase in resistance to flow into the top waste reservoir is due in part to additional energy being necessary to displace the fluid already present in the top waste reservoir. In addition, as will be discussed, the depth of the top waste reservoir increases slightly at the far end away from the sample application port, so when the fluid fills to the far end, the capillary driving force decreases with the increasing depth.

The increasing depth of the top waste reservoir is shown in FIG. 3, which is a cross-sectional view along line 3—3 in FIG. 1. The floor 36 of top waste reservoir 30 angles at a slight angle downwardly to the back wall 38 of top waste reservoir 30. Conveniently, an angle of about 3.7° serves to provide the desired reduction in capillary force.

As the top reservoir fills, both the added resistance to flow towards the top waste reservoir and the decrease in capillary driving force begin to offset the decrease in the capillary driving force of flow into the side waste reservoir 28, and the fluid begins to flow over the 50° slope into the side waste reservoir. This lateral flow washes out any residual sample that was at the edges of the platform 23 and fills the incubation area 22 with substrate. The reaction then occurs in the incubation area 22 and can be read by an instrument, as appropriate.

Where the disposable device comprises the mixing implement, the placement of vertical and trapezoidal ridges on either side of the incubation area serve to constrain fluid in the incubation area. Thus, the capillary force influencing fluid flow in the device again remains constant in the forward direction toward the top waste reservoir. When liquid is added to the side reagent reservoir, the liquid flows over the vertical ridge, across the incubation area and into the side waste reservoir over the ridge having a trapezoidal cross section.

In FIG. 4 is a cross-sectional view of the device in FIG. 1 depicting the slope in the main capillary channel comprising the first flow path. The transport channel 20 slopes at a 45° angle from the beginning of the transport channel below the sample addition port (not shown) to the sample incubation area 22 above platform 23. The remainder of the first flow path is then level from the platform 23 to the top waste reservoir 30.

Figure 5:
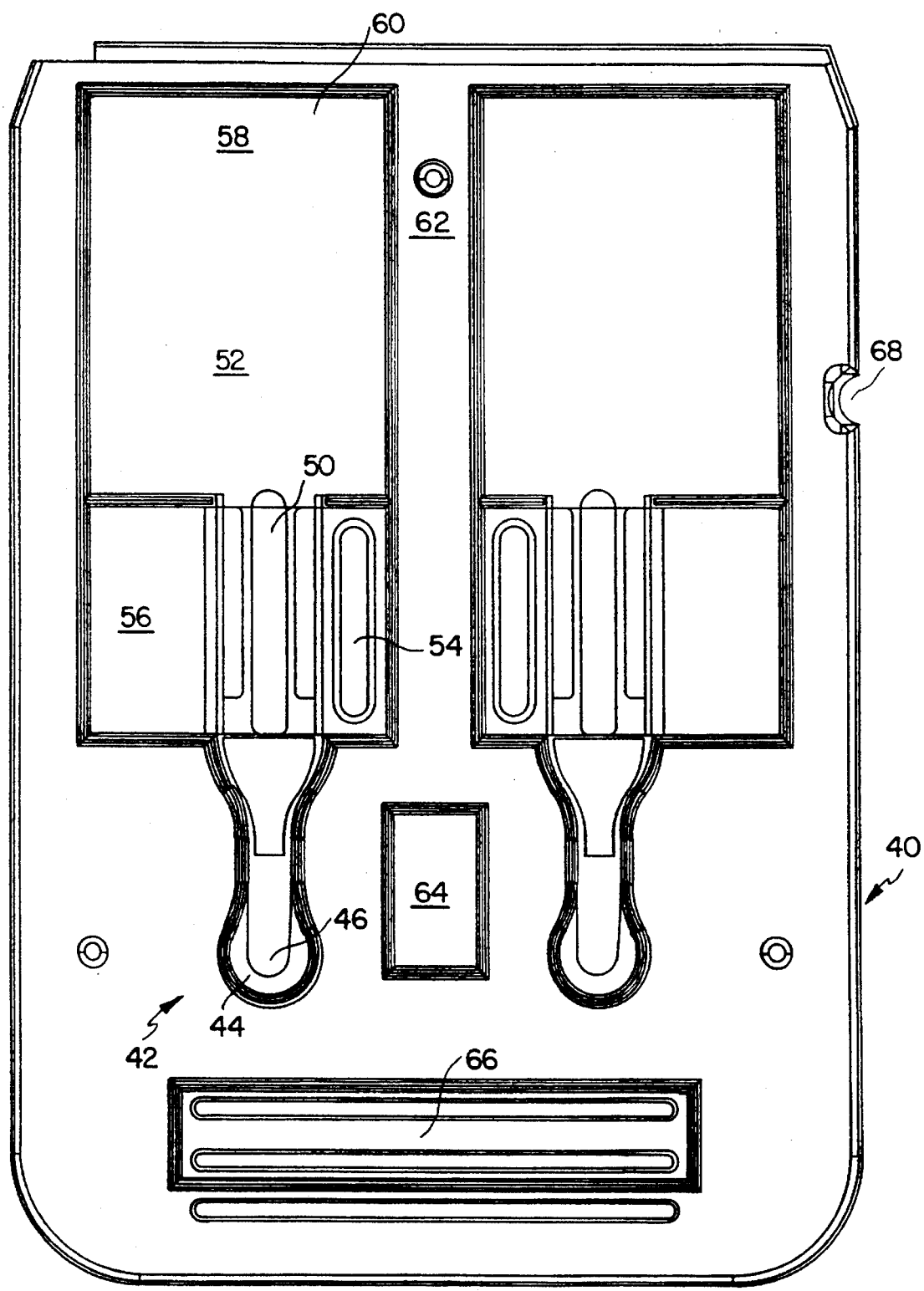
FIG. 5 is a plan view of the bottom housing plate of the disposable device according to FIG. 1.

In FIG. 5 is shown a plan view of the bottom housing plate 40 of the disposable device. The port area 42 has ledge 44 and depression 46. The transport channel 48 maintains a constant depth through the platform reaction area 50 until emptying into top waste reservoir 52. Over reaction area 50 is fluorescent lipid membrane 51. The transport channel 48 will generally be depressed from the surface of the bottom housing 40. On one side of the platform area 50 is the side reagent reservoir 54. On the floor of side reagent reservoir 54 is reagent 55. On the other side is the side waste reservoir 56. As discussed above, the top waste reservoir gradually descends further from the plane of the top surface of the bottom housing 40 in the region 58 approaching the end wall 60 of the top waste reservoir 52. First and second detents, 62 and 64, are provided for registry of the bottom housing with a top housing.

A trough 66 is provided which serves to collect priming liquid from the instrument, when the disposable device is used in conjunction with an instrument which requires liquid priming of conduits located in the instrument. For example, some instruments use a priming liquid which is employed in the conduits of the instrument that are subsequently used to introduce liquid into the disposable device. When such a priming liquid is used, the liquid is collected from the instrument in trough 66 of the disposable device. In this way, the instrument in which the disposable device is used need not have an internal reservoir, since each disposable device will carry away the priming liquid used in a particular instrument prior to the actual assay. The back of the trough 66 has ridges, not shown, which serve to make the cartridge easier to hold. A notch 68 serves to register the device in an instrument for reading the results, where a spring-loaded ball beating may lock the device in place.

Figure 6:
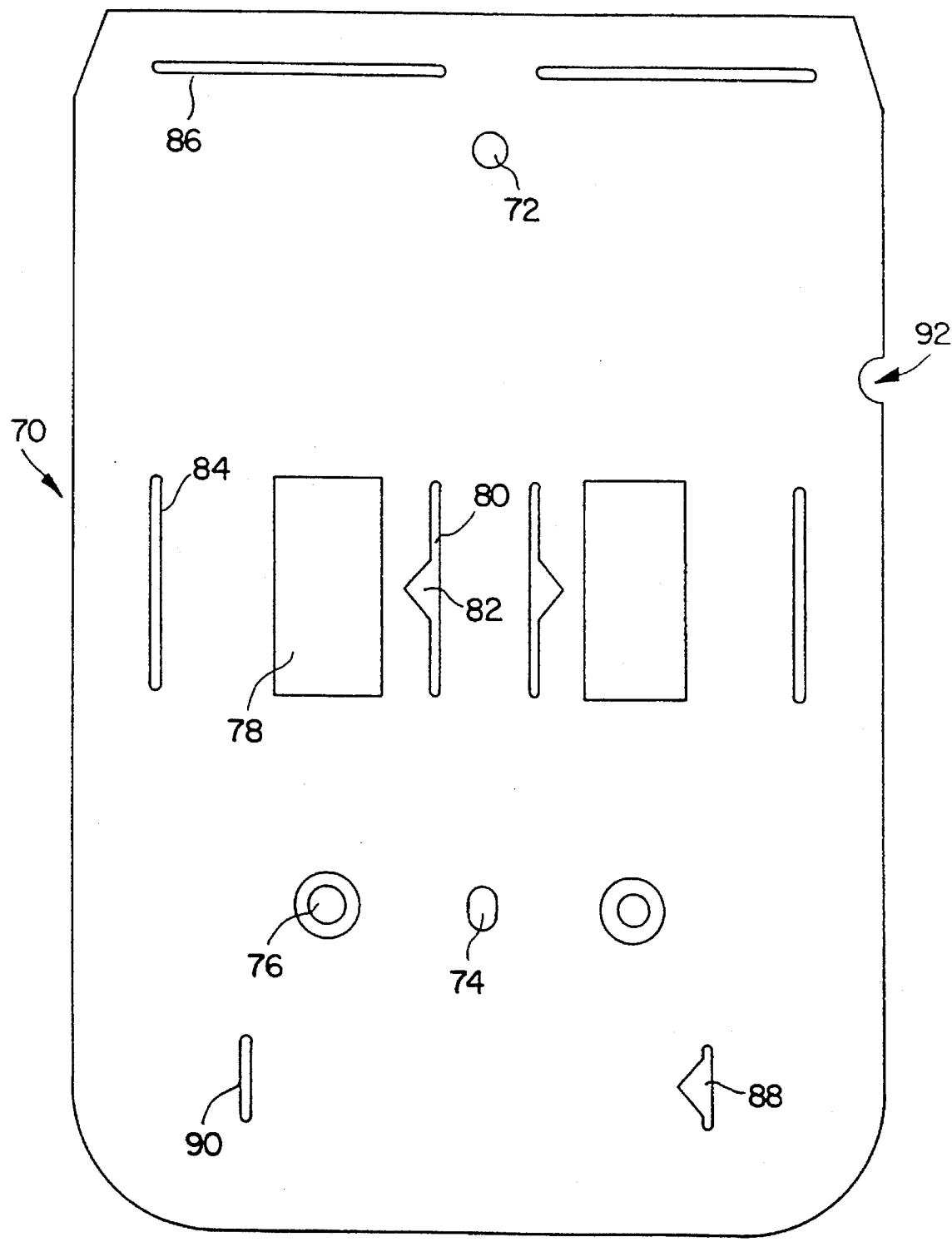
FIG. 6 is a plan view of a top housing plate of the disposable device depicted in FIG. 1.

In FIG. 6 is depicted the top housing plate 70 having first and second apertures, 72 and 74, for receiving detents 62 and 64, respectively. Since the two assay members in the housing are the same, as described previously, only the components of one of the assay members will be described.

A sample port 76 is provided to be in register over the port area 42 and depression 46. The sample port 76 forms a inverted truncated cone, so as to be able to hold the liquid sample as it feeds the liquid into the channel. The optical window 78 is depressed from the plane of the upper surface of the top plate in order to keep the window from being damaged or scratched. Desirably, except for the window 78, the outer surfaces of the bottom and top housings are textured, so as to be translucent. Optical window 78 is in position directly above incubation area 50, while on one side and above the reagent reservoir 54 is addition port 80 which is shaped like a slot having a triangular opening 82 to fit with means for adding buffer solution. An air port or vent 84 is provided to allow for the escape of air as liquid passes from the reagent reservoir 54 over the platform area 50 to the side waste reservoir 56. The use of slots as port vents serves to ensure smooth, uniform spreading of the fluids. A second air port 86 is provided for escape of air from the top waste reservoir 52. A notched port 88 provides access to trough 66, which also has an air port 90. A notch 92, which has a different conformation from the notch 68 of the bottom housing, is in registry with notch 68 and provides space for a ball bearing to lock the device into place.

Figure 7:
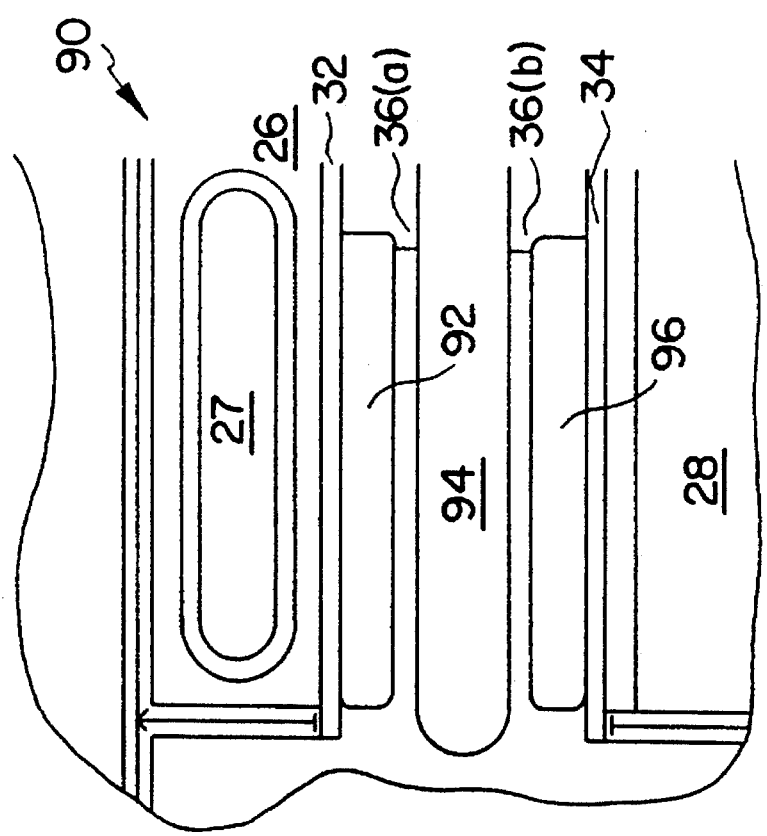
FIG. 7 is a detailed view of the platform in the disposable device comprising the mixing implement.

In FIG. 7 is a top view of the second flow path of the disposable device comprising an agitation means in the incubation area. The second flow path begins at the side reagent reservoir 26. The reagent in the side reagent reservoir is specifically stored in a depressed trough 27 on the floor of the reservoir. Across vertical ridge 32 lies the first dry reagent trough 92. Dry reagent trough 92 is separate from mixing implement trough 94 by ridge 36(a). The mixing implement trough 94 houses the mechanical mixing implement (not shown). Across ridge 36(b) lies the second dry reagent trough 96. Finally, across ridge 34 having a trapezoidal cross section lies side waste reservoir 28.

Figure 8:
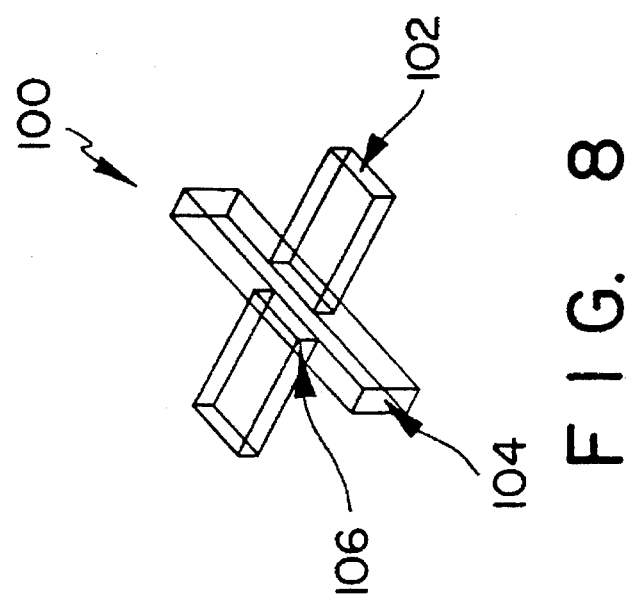
FIG. 8 is an overhead, three dimensional view of a capillary valve.

In FIG. 8 is depicted an overhead, three dimensional view of the capillary valve that may be positioned adjacent to the incubation area to control flow through the incubation area. Capillary valve 100 comprises fluid flow capillary channel 102 and control capillary 104 at fight angles to each other, so that control capillary 104 intersects fluid capillary channel 102 at intersection 106. This intersection disrupts fluid flow in flow capillary channel 102 when control capillary 104 is empty, but does not impede fluid flow through flow capillary channel 102 when it is full.

The capillary channel may be placed in a variety of positions in the fluid flow path of the device in order to enhance control of fluid flow through the device. For example, if enhanced control of fluid flow from the side reagent reservoir to the incubation area is desired, the capillary valve 106 will be positioned in the disposable device between the side reagent reservoir and the incubation area. Flow capillary channel 102 would correspond to the channel between the side reagent reservoir and the incubation area, while the control capillary 104 would run parallel to the edge of the incubation area thus intersecting flow capillary channel 102.

To assemble the device, the appropriate reagents are placed at their proper sites, e.g. coating the surface of the dry reagent troughs. The membrane is placed in the incubation upper surface area, substrate, as appropriate, in the side reagent reservoir and conjugate (dry reagent) is placed on the trough platform floor immediately beneath the window or, if appropriate, coated on the trough surfaces. The membrane is readily transferred to the top housing surface under the window by conventional means. After the reagents have been positioned, the top housing can be placed in registry over the bottom housing and the edges sealed by any appropriate means, such as ultrasonic welding, adhesives, etc. The device is then ready to be stored for subsequent use. Since two assays can be run, the two assay members can be used for a single assay and a control, for the same assay for two samples, or two different assays for the same or different samples. Thus, various configurations of protocols may be employed depending upon the nature of the desired assays. In addition, one may have a device with a single assay or a plurality of assays greater than two and one can vary the size appropriately, in accordance with the number of assays involved.

It is evident from the above description, that a convenient disposable assay device is provided, where one can provide for automatic addition of samples and washes, so that assays may be carried out substantially automatically. Thus, the technical requirements of the operation are quite minimal for operation and one can obtain reproducibility and accuracy with very high sensitivity. The devices are easily stored, being flat and thin, so that large packages of devices can be readily transported. The reagents are protected from contamination particularly where the device can be wrapped, so as to insure the substantial absence of moisture and air getting into the device.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A diagnostic disposable device comprising:

a housing;

said housing comprising an assay system comprising:

a fluorescent lipid membrane, wherein proximal to one face of said fluorescent lipid membrane is a member of a specific binding pair;

an incubation area in said housing, having spaced apart top and bottom surfaces to provide for capillary flow through said incubation area: said top surface supporting said fluorescent lipid membrane; said bottom surface capable of supporting a reagent which specifically binds to the specific binding pair member of said fluorescent lipid membrane or said analyte during an assay, reservoirs connected to each side of said incubation area said reservoirs being a side reagent reservoir having an inlet port and a side waste reservoir, wherein said bottom surface is raised above said side reagent and waste reservoirs and side walls extend from said bottom surface to said side reagent and waste reservoirs;

proximal to one end of said housing, a sample port;

a capillary channel connecting said incubation area and said sample port;

a top waste reservoir downstream from said incubation area opposite from said capillary channel, said top and side waste reservoirs having gas release port; and an optically clear window over said fluorescent lipid membrane for viewing.

2. A diagnostic disposable device according to claim 1, wherein said side walls of said bottom surface extending from said bottom surface drop steeply down to said side reservoirs to substantially reduce capillary force.

3. A diagnostic disposable device according to claim 1, wherein said bottom surface comprises agitation means, wherein said agitation means are positioned in a mixing implement trough.

4. A diagnostic disposable device according to claim 3, wherein said bottom surface further comprises dry reagent troughs running parallel with said mixing implement trough, wherein the walls of said dry reagent troughs are coated with dry reagent.

5. A diagnostic disposable device according to claim 1, wherein said housing has a trough, an inlet port and a gas release port for said trough, unconnected with said assay system for receiving priming or other waste fluid.

6. A diagnostic disposable device according to claim 1, wherein the depth of said top waste reservoir increases distal from said incubation area.

7. A diagnostic disposable device according to claim 1, said device further comprising a capillary valve positioned adjacent to said incubation area for controlling said capillary flow through said incubation area.

8. A diagnostic disposable device comprising:

a housing;

said housing comprising a top plate and bottom plate fastened together, one plate having detents and the other plate having orifices for indexing said plates;

said housing containing an assay system comprising:

a fluorescent lipid membrane, wherein proximal to one face of said fluorescent lipid membrane is a member of a specific binding pair;

an incubation area in said housing, having top and bottom surfaces, said top surface supporting said fluorescent lipid membrane and said bottom surface supporting a reagent which specifically binds to the specific binding pair member of said fluorescent lipid membrane during an assay, said surfaces being spaced apart to provide for capillary flow through said incubation area;

said bottom surface comprising agitation means in a mixing implement trough and two dry reagent troughs running parallel with said mixing implement trough, wherein dry reagent coats the surface of said troughs;

proximal to one end of said housing, a sample port;

a capillary channel connecting one side of said incubation area to said sample port;

side reservoirs on each side of said incubation area, said side reservoirs being a side reagent reservoir and a side waste reservoir on opposite sides of said incubation area, and a top waste reservoir downstream from said incubation area opposite from said capillary channel, said top waste reservoir and said side waste reservoir having gas release ports, said side reagent reservoir having an inlet port, said gas release ports being slots extending along one side of said top and side waste reservoirs; and an optically clear window over said fluorescent lipid membrane for viewing.

9. A diagnostic disposable device according to claim 8, wherein said dry reagent interacts with said specific binding pair member proximal to one face of said fluorescent lipid membrane.

10. A diagnostic disposable device according to claim 9, wherein said reagent is an enzyme conjugate and said side reagent storage reservoir contains enzyme substrate.

11. A diagnostic disposable device according to claim 8, wherein said housing comprises a plurality of assay systems.

12. A diagnostic disposable device according to claim 8, wherein said housing has a trough, an inlet port and a gas release port for said trough, unconnected with said assay system housed in said diagnostic disposable device, wherein said trough serves for receiving priming or other waste fluid from an instrument housing said diagnostic disposable device And is in a fluid collecting relationship with said instrument.

13. A diagnostic disposable device according to claim 8, wherein the depth of said main waste reservoir increases distal from said incubation area.

14. A diagnostic disposable device according to claim 8, wherein said plates are made of a moldable plastic and said plates are welded together.

15. A diagnostic disposable device according to claim 8, wherein said device further comprises a capillary valve positioned adjacent to said incubation area for control of said capillary flow through said incubation area.

16. A method for determining an analyte in a sample, said method comprising:

providing disposable diagnostic device comprising:
  a housing;
  said housing comprising an assay system comprising:
  a fluorescent lipid membrane wherein proximal to one face of said fluorescent lipid membrane is a member of a specific binding pair;
an incubation area in said housing having spaced apart top and bottom surfaces to provide for capillary flow through said incubation area; said top surface supporting said fluorescent lipid membrane: said bottom surface supporting an enzyme conjugate reagent which specifically binds to the specific binding pair member of said fluorescent lipid membrane during an assay reservoirs connected to each side of said incubation area said reservoirs being a side reagent reservoir having an inlet port and a side waste reservoir;
proximal to one end of said housing, a sample port;
a capillary channel connecting said incubation area and said sample port;
a top waste reservoir downstream from said incubation area opposite from said capillary channel; and
an optically clear window over said fluorescent lipid membrane for viewing;
adding sample to the sample port of said disposable diagnostic device;
allowing said sample to move through said incubation area, whereby said enzyme conjugate is dissolved and binds to said member of the specific binding pair of said fluorescent lipid membrane in proportion to the amount of analyte present in said sample;
washing said incubation area to wash said incubation area substantially free of sample components and unbound conjugate;
introducing a solution containing enzyme substrate into said incubation area, whereby enzyme product is produced which modulates the fluorescence of said fluorescent lipid membrane;
irradiating said fluorescent lipid membrane through an optically clear window over said fluorescent lipid membrane, whereby said lipid membrane is excited and fluoresces; and
measuring the fluorescence intensity at least one time to determine the presence of analyte in said sample.

17. A method according to claim 16, wherein said analyte is a hapten.

18. A method according to claim 16, wherein said analyte is an antigen.

19. A method according to claim 16, wherein said analyte and said enzyme conjugate are competitive in binding to the specific binding pair member of said fluorescent lipid membrane.

20. A method according to claim 16, wherein said analyte bridges the specific binding pair member of said fluorescent lipid membrane and said conjugate.

21. A method according to claim 16, wherein said method further comprises agitating said sample in said incubation area.

22. A diagnostic disposable device comprising:

a housing, said housing comprising:
an incubation area having spaced apart top and bottom surfaces to provide for capillary flow through said incubation area;
proximal to one end of said housing, a sample port;
a capillary channel connecting one side of said incubation area to said sample port;
reservoirs connected to each remaining side of said incubation area, said reservoirs comprising a side reagent reservoir and a side waste reservoir on opposite sides of said incubation area, and a top waste reservoir opposite from said transport channel, said top and side waste reservoirs having gas release ports, with said side reagent reservoirs having an inlet port to allow for flow of liquid orthogonal to the flow direction defined by said capillary channel;
reagent members of a signal producing system, wherein at least one of said members is present in said incubation area; and
an optically clear window over said incubation area for viewing.

* * * * *